United States Patent
DeNoble et al.

(10) Patent No.: US 11,981,520 B2
(45) Date of Patent: *May 14, 2024

(54) APPARATUS AND METHOD FOR WEB TWIST DEFECT CORRECTION

(71) Applicant: Curt G. Joa, Inc., Sheboygan Falls, WI (US)

(72) Inventors: Adam D. DeNoble, De Pere, WI (US); Jeffrey Dale Brown, Sheboygan, WI (US); Robert E. Andrews, Falmouth, ME (US); Gottfried Jason Hohm, Oconomowoc, WI (US); Dennis J. Faucher, Sheboygan, WI (US)

(73) Assignee: CURT G. JOA, INC., Sheboygan Falls, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 17/304,035

(22) Filed: Jun. 14, 2021

(65) Prior Publication Data
US 2021/0300707 A1    Sep. 30, 2021

Related U.S. Application Data

(63) Continuation of application No. 16/401,231, filed on May 2, 2019, now Pat. No. 11,034,539, which is a
(Continued)

(51) Int. Cl.
*B65H 23/032* (2006.01)
*A61F 13/15* (2006.01)
(Continued)

(52) U.S. Cl.
CPC ....... *B65H 23/00* (2013.01); *A61F 13/15772* (2013.01); *D06B 23/08* (2013.01);
(Continued)

(58) Field of Classification Search
CPC .......... B65H 23/00; B65H 2301/33224; B65H 2553/42; B65H 2801/57; A61F 13/15772; D06B 23/08
(Continued)

(56) References Cited

U.S. PATENT DOCUMENTS 4,174,567 A    11/1979   Kamoshida et al.
5,992,318 A *  11/1999   DiBello .............. B41F 33/0045
                                                 101/DIG. 45
(Continued)

FOREIGN PATENT DOCUMENTS

EP    1433731 A1    6/2004
EP    2639066 A2 *  1/2019

*Primary Examiner* — Albert Kir
(74) *Attorney, Agent, or Firm* — Quarles & Brady, LLP

(57) ABSTRACT

Apparatus and methods are provided to minimize waste and improve quality and production in web processing operations. The apparatus and methods provide defect detection in deposition of acquisition material, which on current machines frequently flips and is difficult to detect when it has flipped causing manufacturers to scrap thousands of products. Using the present invention, defects are able to be
(Continued)

detected by discerning a difference in the appearance from side to side with a vision camera, and an acquisition inverter can flip the material to a correct orientation.

26 Claims, 8 Drawing Sheets

Related U.S. Application Data continuation of application No. 13/414,393, filed on Mar. 7, 2012, now abandoned.

(60) Provisional application No. 61/450,990, filed on Mar. 9, 2011.

(51) Int. Cl.
    *B65H 16/00*     (2006.01)
    *B65H 19/22*     (2006.01)
    *B65H 23/00*     (2006.01)
    *D06B 23/08*     (2006.01)

(52) U.S. Cl.
    CPC .............. *B65H 2301/33224* (2013.01); *B65H 2553/42* (2013.01); *B65H 2801/57* (2013.01)

(58) Field of Classification Search
    USPC ...................................................... 348/88, 86
    See application file for complete search history.

(56) References Cited

U.S. PATENT DOCUMENTS

| | | | |
|---|---|---|---|
| 6,006,669 A | 12/1999 | Klein et al. | |
| 6,112,658 A * | 9/2000 | Gunther | B26D 5/007 |
| | | | 101/171 |
| 9,428,360 B2 * | 8/2016 | Herrmann | B65H 23/032 |
| 9,603,752 B2 * | 3/2017 | Brown | B65H 23/032 |
| 11,325,801 B2 * | 5/2022 | Follen | B65H 19/123 |
| 2003/0120714 A1 | 6/2003 | Wolff et al. | |
| 2004/0223053 A1 * | 11/2004 | Gladnick | G06T 1/0007 |
| | | | 348/86 |
| 2009/0020211 A1 * | 1/2009 | Andrews | A61F 13/15699 |
| | | | 156/379 |
| 2009/0141987 A1 | 6/2009 | McGarry et al. | |
| 2009/0273668 A1 | 11/2009 | Mirtich et al. | |
| 2014/0104360 A1 * | 4/2014 | Hacker | B41J 3/60 |
| | | | 347/104 |
| 2014/0209655 A1 * | 7/2014 | Haque | B65H 23/038 |
| | | | 226/15 |
| 2014/0364031 A1 * | 12/2014 | Haley | D04H 3/004 |
| | | | 442/388 |
| 2019/0263153 A1 * | 8/2019 | Wakabayashi | B41J 15/04 |
| 2021/0394386 A1 * | 12/2021 | Acciari | B26D 7/2635 |

* cited by examiner

APPARATUS AND METHOD FOR WEB TWIST DEFECT CORRECTION

CROSS-REFERENCE TO RELATED APPLICATIONS

This application is a continuation of and claims priority to U.S. patent application Ser. No. 16/401,231, filed 2 May 2019, which is a continuation of and claims priority to U.S. patent application Ser. No. 13/414,393, filed 7 Mar. 2012, which claims priority to U.S. Provisional Patent Application Ser. No. 61/450,990, filed 9 Mar. 2011, the disclosures of which are incorporated herein by reference in their entirety.

BACKGROUND OF THE INVENTION

The invention disclosed herein relates to apparatus and methods for waste reduction and improvements to the quality and production in web processing operations, such as diaper manufacturing. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form and are unwound and applied in assembly line fashion.

One such layer, the acquisition layer, is used to more evenly distribute liquid insults to disposable products. In modern disposable products, super absorbent polymers (SAP) are used to store liquid. SAP is generally excellent at liquid storage, but because SAP turns to a gelatinous type material, does not distribute liquid well. Therefore, an acquisition layer plays a key role in dispersing liquids away from the point of deposit in order to increase the overall liquid storage capacity of the SAP. Because the acquisition layer performs better when oriented properly, it is important that the layer be deposited into the disposable product uniformly and correctly oriented.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition web material and a nonwoven web material, both of which are fed from material rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a die roller and a platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs: a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slicing is twofold. First, the nonwoven web is separated into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners.

After the nonwoven web is sliced, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed. A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator while the stopped web material in the accumulator can be spliced to the standby roll. Examples of web accumulators include that disclosed in U.S. patent application Ser. No. 11/110,616, which is commonly owned by the assignee of the present application and incorporated herein by reference.

As in many manufacturing operations, waste minimization is a goal in web processing applications, as products having spliced raw materials cannot be sold to consumers. Indeed, due to the rate at which web processing machines run, even minimal waste can cause inefficiencies of scale. In present systems, waste materials are recycled. However, the act of harvesting recyclable materials from defective product is intensive. That is, recyclable materials are harvested only after an identification of a reject product at or near the end of a process. The result is that recyclable materials are commingled, and harvesting requires the extra step of separating waste components. Therefore, the art of web processing would benefit from systems and methods that identify potentially defective product prior to product assembly, thereby eliminating effort during recyclable material harvesting.

Furthermore, to improve quality and production levels by eliminating some potentially defective product, the art of web processing would benefit from systems and methods that ensure higher product yield and less machine downtime.

In some applications, narrow webs of material are introduced into the manufacturing process. Narrow webs can get twisted because they can jump rollers in the system. If the narrow webs become twisted, the twist often persists in the form of an undesirable overlap of material. This often has required operators to undesirably stop the machine and manually remove the twist from the web.

SUMMARY OF THE INVENTION

Provided are method and apparatus for minimizing waste and improving quality and production in web processing operations.

Importantly, the methods taught in the present application are applicable not only to diapers and the like, but in any web-based operation. The waste minimization techniques taught herein can be directed any discrete component of a manufactured article, i.e., the methods taught herein are not product specific. For instance, the present methods can be applied as easily with respect to diaper components as they can for feminine hygiene products, as they can for face masks in which components such as rubber bands and nose pieces are used.

For instance, by practicing the methods of the present invention, waste of staples and elastic bands can be avoided during manufacture of face masks, for instance those disclosed in U.S. Pat. No. 7,131,442. One of the objectives is simply to recognize product during manufacture that ultimately would fail quality control inspection and avoid placing material onto that product during the manufacturing processes.

As another example, the amount of adhesive applied to certain products can be reduced by not applying adhesive to products that have already been determined to be defected or assigned to rejection. For instance, in U.S. Pat. No. 6,521,320, adhesive application is shown for example in FIG. 11. By assigning or flagging product that has already been determined to end up in a scrap or recycling pile, the adhesive flow can be stopped or minimized.

In yet another exemplary application of the methods of the present invention, discrete components or raw material carried on products that have already been determined to be defected or assigned to rejection can also be removed and recycled prior to commingling with other discrete components or raw material. For instance, if an absorbent pad, such as shown at reference numeral 40 of U.S. Pat. No. 6,521,320 is destined for application to a product that has already been determined to be defected or assigned to rejection, the absorbent pad can be withdrawn from the product, or never introduced in the first instance. For example, during startup or shutdown of high-speed diaper manufacturing operations, a certain number of products are routinely discarded into recycling. By identification of the startup or shutdown routine, avoidance of introduction of absorbent pads can be achieved. Alternatively, during standby, the absorbent pads often degrade by accumulation of dust. By identifying which products would bear the dust, the absorbent pads can be withdrawn from further manufacture, and no additional components would be applied to such a product.

In one embodiment, a method for assembling a plurality of continuous webs is provided, including defining first web inspection parameters and inspecting at least one of the plurality of continuous webs to determine whether the at least one web conforms to the first web inspection parameters. Further, the method involves providing a chassis web which is adapted to receive a patch and providing a patch web from which the patch is cut. Finally, the cut patch is applied to the chassis web if the inspected web conforms to the first web inspection parameters. In another embodiment, the method also includes steps of defining first patch inspection parameters and inspecting a cut patch to determine whether the patch conforms to the first patch inspection parameters. While the patch inspection may provide interesting diagnostic information related to a web processing machine, the application of the patch may be limited to those patches that conform to the first patch inspection parameters.

Another embodiment of the method of the present invention involves defining first web inspection parameters and a product pitch. Generally in any web process, a web is provided, which is traveling at a web velocity. This embodiment involves inspecting the web to determine whether the web conforms to the first web inspection parameters and producing an inspection value as a result of the inspecting step. This value is then recorded once per sample time interval. The sample time interval may be calculated by dividing the defined product pitch by the web velocity. While the inspection value may be as simple as a bivalent value, a more informational multivalent value may be used.

In addition to the web process provided, an apparatus for carrying out the process is provided. An embodiment of the apparatus includes a continuous web supply providing continuous web material from an upstream position to a downstream position and a means for providing a patch spaced from a first side of the continuous web material. A patch applicator is provided to alter the space between the patch providing means and the continuous web material and a web inspection device is positioned upstream from the patch applicator. Additionally, a programmable controller receives an input from the web inspection device and provides an output to the patch applicator. The web processing apparatus may also include a patch inspection device that provides an output to the programmable controller. A patch reject conveyor may be positioned to receive defective patches from the patch providing means. In another embodiment of a web processing apparatus, a product inspection device may be located downstream from the patch applicator to provide an output to the programmable controller. Also, a product reject conveyor could be adapted to divert defective product as indicated by the product inspection device.

In another aspect of the invention, twists in narrow webs, such as an acquisition layer, are first recognized and then self-corrected, resulting in a scrap reduction. A camera or other type of vision system first detects a twist (or the acquisition layer being deposited in an upside-down manner), and next when a twist is seen, a narrow web turning device flips the web, to get the twist out and return the web to its properly oriented deposit position.

A web inverter is positioned based on process constraints. Flipping of spooled material occurs most frequently as it is unwound of the roll, and this requires correction by inverting the web to its properly oriented condition. Repeated faults within a predetermined time period could force a shutdown to investigate a potential problem. Twists are detected prior to application with a vision camera. These twists most frequently occur as the spooled material is unwound. It is preferred to look for and detect the correct orientation immediately prior to application of the material onto downstream processes.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present waste minimization techniques and apparatus are described herein with respect to products such as diapers, but as previously mentioned, can be applied to a wide variety of processes in which discrete components are applied sequentially.

Figure 1A:
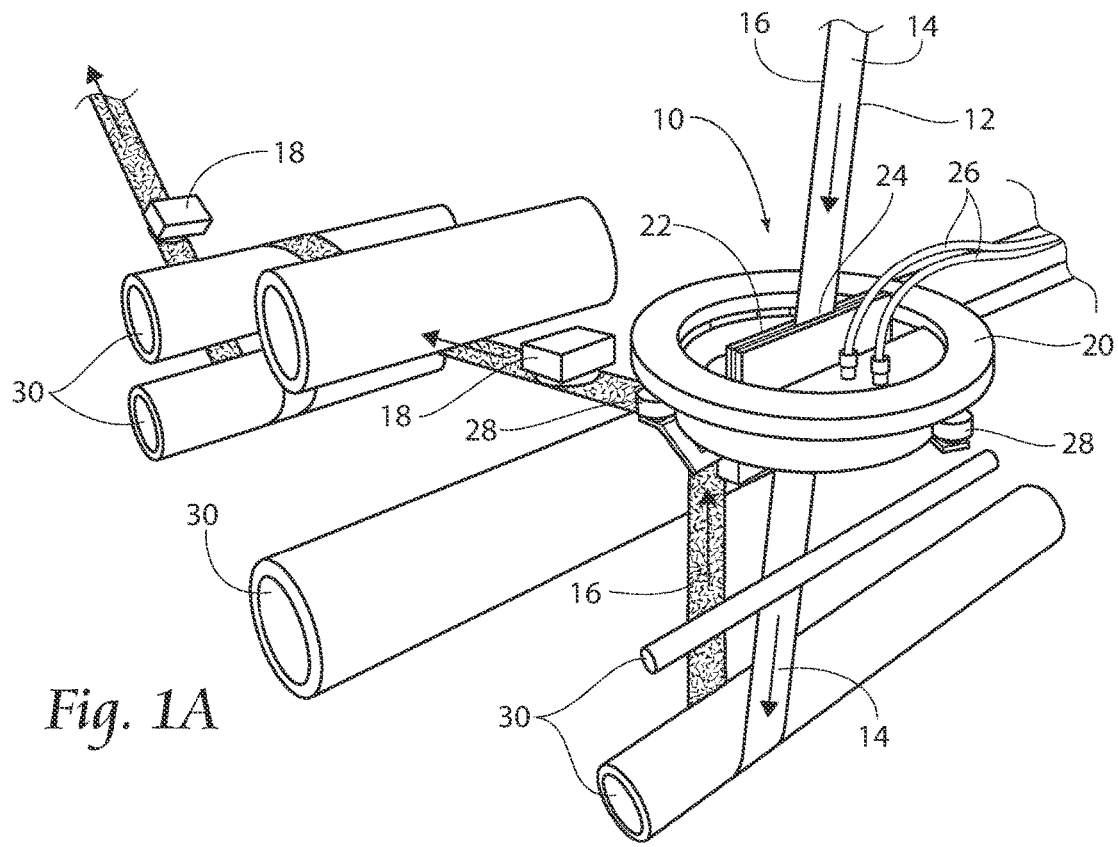
FIG. 1A is a perspective view of a web processing system of the present invention, carrying a web in a properly oriented condition.

Referring now to FIG. 1A, a perspective view of a web processing system 10 of the present invention is shown, carrying a web 12 (such as an acquisition layer) in a properly oriented condition. In its properly oriented condition, side 16 is visible from the top, side 14 is visible from the bottom.

As seen on FIG. 1A, at vision inspection locations 18, inspection can take place to determine the presence or absence of acceptable product introduction. In this case, acceptable product introduction would be either that side 16 is visible from the top, and/or that the web 12 is not twisted and remains at its proper web width.

In addition to visual inspection, operational characteristics such as startup/ramp-up/shutdown operations can trigger waste minimization techniques as will be described later.

At each of these vision stations 18 shown in FIG. 1, diagnostics can be performed to indicate whether the product meets acceptable criteria. If so, discrete elements, such as the core, tissue layers, elastic, etc., continue to be applied in a sequence as desired. If not, no additional discrete elements need be applied.

In addition to the exemplary components generally found in a web processing apparatus, the present device and methods further include an advanced defect detection system. An embodiment of the defect detection system preferably comprises at least one visual inspection station 18, but preferably a plurality of visual inspection stations 18. Each visual inspection station 18 may include a vision sensor, such as an In-Sight Vision Sensor available from Cognex Corporation of Natick, Mass. Since each component part of a product resulting from a web process has a point of incorporation into the product, visual inspection of each component part preferably occurs prior to the point of incorporation. The results of the visual inspections that occur are relayed from each visual inspection station 101 to a programmable logic controller (PLC) (not shown). Each visual inspection station 18 may provide diagnostic capability by monitoring lighting, focus and positioning.

Machine vision systems typically require digital input/output devices and computer networks to control other manufacturing equipment, in this case the correction sequence initiated by rotation of ring 20.

A typical machine vision system will consist of several among the following components:

One or more digital or analog camera (black-and-white or color) with suitable optics for acquiring images Lighting Camera interface for digitizing images (widely known as a "frame grabber")

A processor (often a PC or embedded processor, such as a DSP)

Computer software to process images and detect relevant features.

A synchronizing sensor for part detection (often an optical or magnetic sensor) to trigger image acquisition and processing.

Input/Output hardware (e.g. digital I/O) or communication links (e.g. network connection or RS-232) to report results Some form of actuators used to sort or reject defective parts.

The sync sensor determines when a part (often moving on a conveyor) is in position to be inspected. The sensor triggers the camera to take a picture of the part as it passes by the camera and often synchronizes a lighting pulse. The lighting used to illuminate the part is designed to highlight features of interest and obscure or minimize the appearance of features that are not of interest (such as shadows or reflections).

The camera's image can be captured by the framegrabber. A framegrabber is a digitizing device (within a smart camera or as a separate computer card) that converts the output of the camera to digital format (typically a two-dimensional array of numbers, corresponding to the luminous intensity level of the corresponding point in the field of view, called pixel) and places the image in computer memory so that it may be processed by the machine vision software.

The software will typically take several steps to process an image. In this case, the image processing will result in either detection of the appropriate side of the web 16, or detection of the incorrect orientation 14 of the web 12.

Commercial and open source machine vision software packages typically include a number of different image processing techniques such as the following:

Pixel counting: counts the number of light or dark pixels

Thresholding: converts an image with gray tones to simply black and white

Segmentation: used to locate and/or count parts

Blob discovery & manipulation: inspecting an image for discrete blobs of connected pixels (e.g. a black hole in a grey object) as image landmarks. These blobs frequently represent optical targets for machining, robotic capture, or manufacturing failure.

Recognition-by-components: extracting geons from visual input

Robust pattern recognition: location of an object that may be rotated, partially hidden by another object, or varying in size Barcode reading: decoding of 1D and 2D codes designed to be read or scanned by machines Optical character recognition: automated reading of text such as serial numbers Gauging: measurement of object dimensions in inches or millimeters Edge detection: finding object edges Template matching: finding, matching, and/or counting specific patterns.

In most cases, a machine vision system will use a sequential combination of these processing techniques to perform a complete inspection. A system that reads a barcode may also check a surface for scratches or tampering and measure the length and width of a machined component.

Additionally, machine downtime can be minimized by the provision of systems and methods for warning a machine operator of expected machine troubles so that scheduled maintenance can occur.

The PLC includes software adapted to run several routines that may be initiated by some triggering event, such as an automatic detection of a defined condition or manual input by a machine operator. Some routines are run during machine setup while other routines are run during machine operation, while still other routines are run during machine diagnostics at some point during machine downtime.

In the present case, the route that the PLC initiates is triggered by detection of the narrow web in an improperly oriented condition. The correction sequence is rotation of ring 20, carrying web guide plates 22.

Figure 1B:
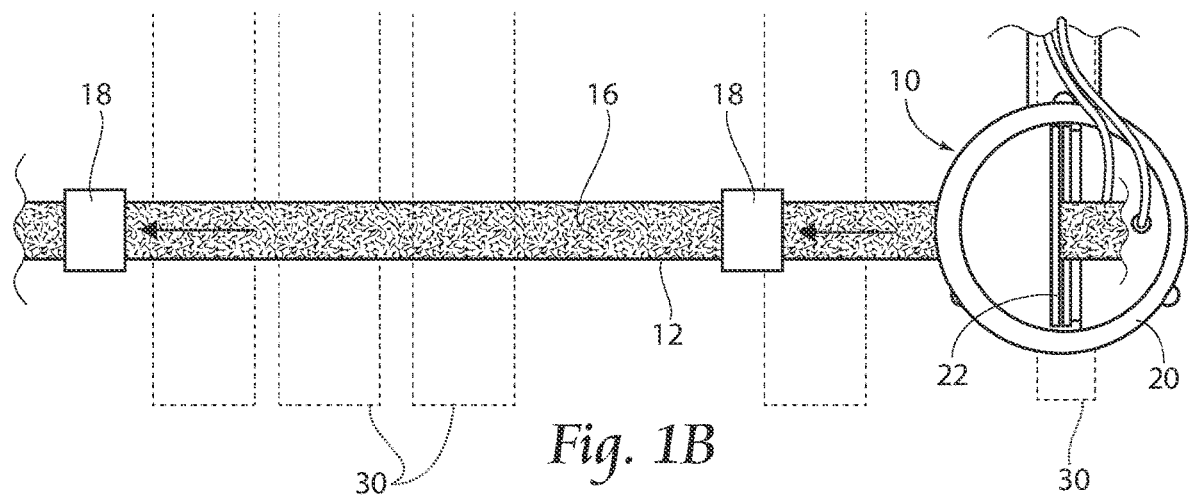
FIG. 1B is a top plan view of the web processing system shown in FIG. 1A, carrying a web in a properly oriented condition.

Referring now to FIG. 1B, a top plan view of the web processing system 10 is shown carrying the web 12 in a properly oriented condition, with side 16 visible from the top. A pair of guide plates 22 carry between them the incoming web 12. The guide plates 22 are preferably actuated between a closed condition and an open condition by pneumatic air lines 26 in order to, in the closed condition, effectuate a twist in the web 12 and, in the open condition, allow splices in the incoming web 12 to pass.

Guide plates 22 are carried by and coupled to rotatable ring 20. Ring 20 is rotatable by any means, such as additional pneumatic or belt driven means (not shown).

Web 12 is passed by a series of rollers 30 and passed downstream for further processing, such as slip/cut application units, introduction onto a disposable product, or intermittent or constant laydown onto other additional webs as desired.

Figure 2A:
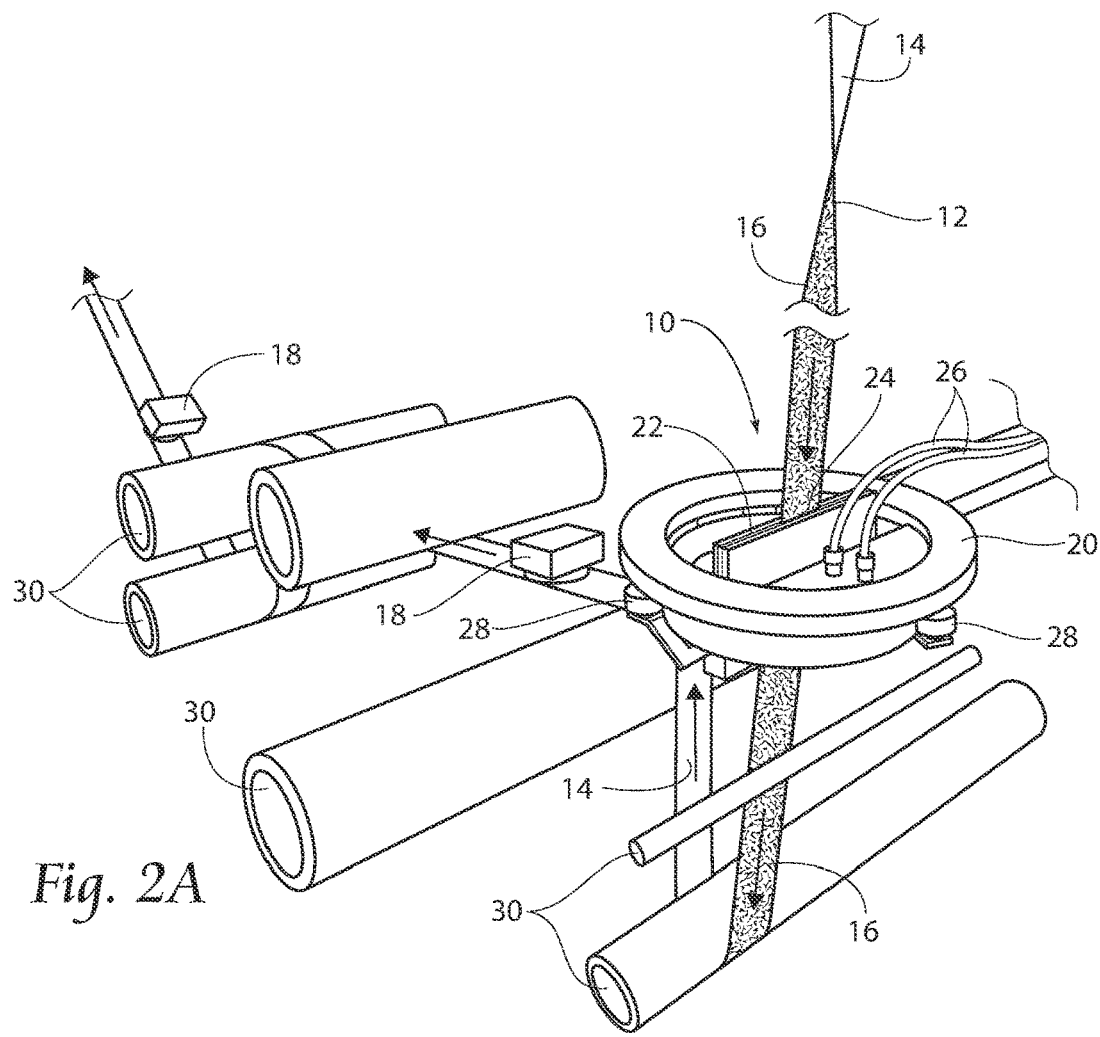
FIG. 2A is a perspective view of a web processing system of the present invention shown carrying a web in a twisted condition.
Figure 2B:
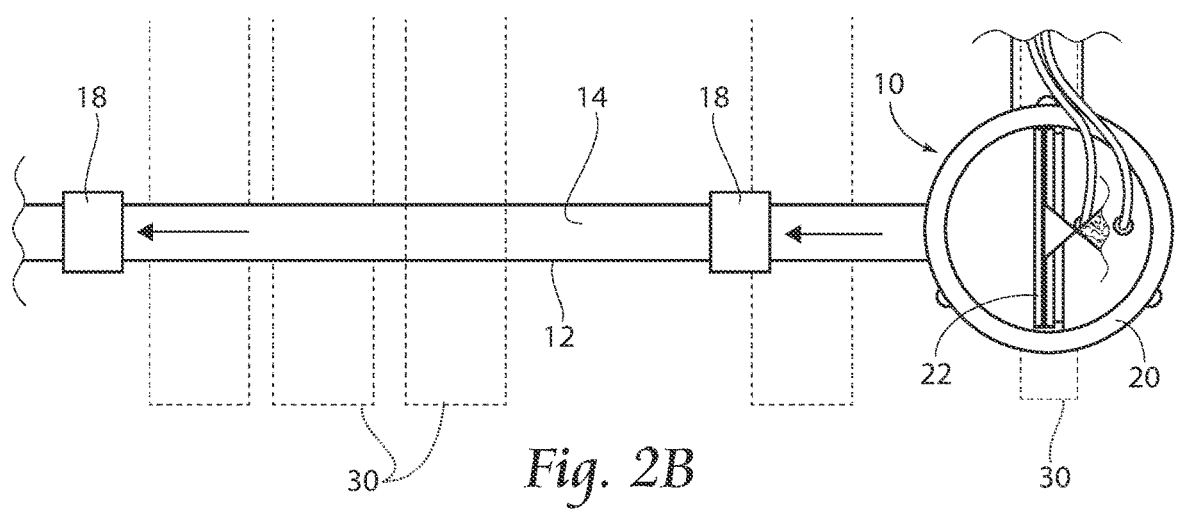
FIG. 2B is a top plan view of the web processing system shown in FIG. 2A, carrying a web in a twisted condition.

Referring now to FIG. 2A, a perspective view of a web processing system 10 is shown carrying web 12 in a twisted condition. As previously noted, the twisting often occurs upstream, or just after the material unwind station (not shown). In this twisted condition, unacceptable product could be produced as the web would be in its incorrect facing orientation. FIG. 2B is a top plan view of this condition.

Figure 3:
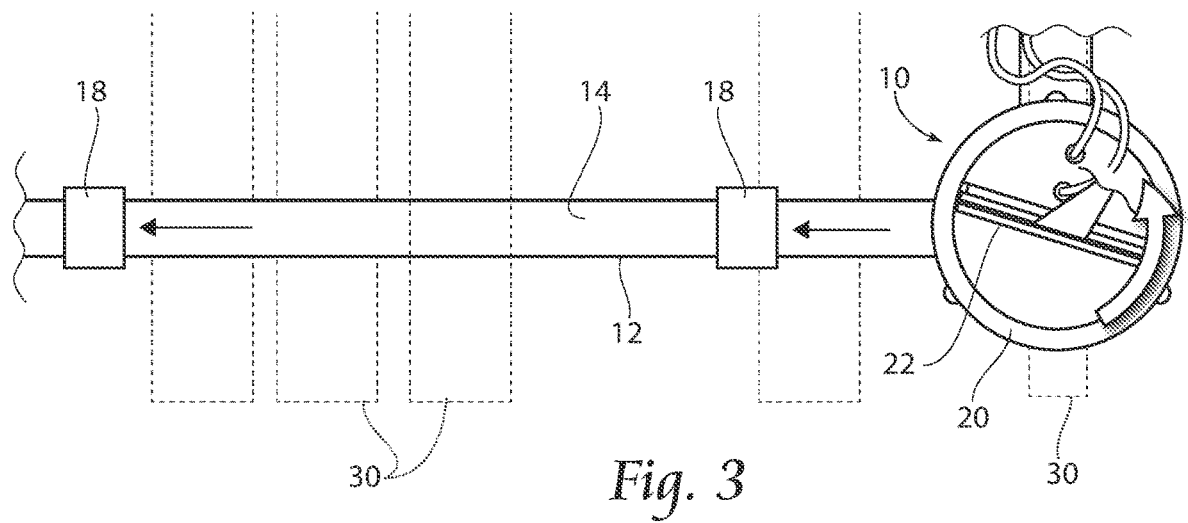
FIG. 3 is a top view of the web processing system shown initiating a correction sequence.
Figure 4:
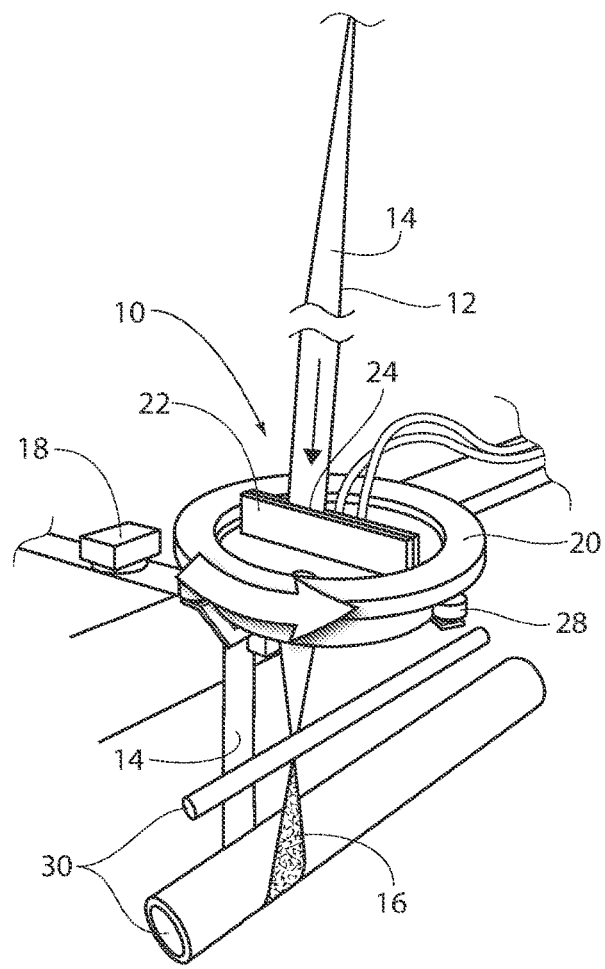
FIG. 4 is a perspective view of FIG. 3, showing the web correction being initiated by imparting a twist to the web.
Figure 5:
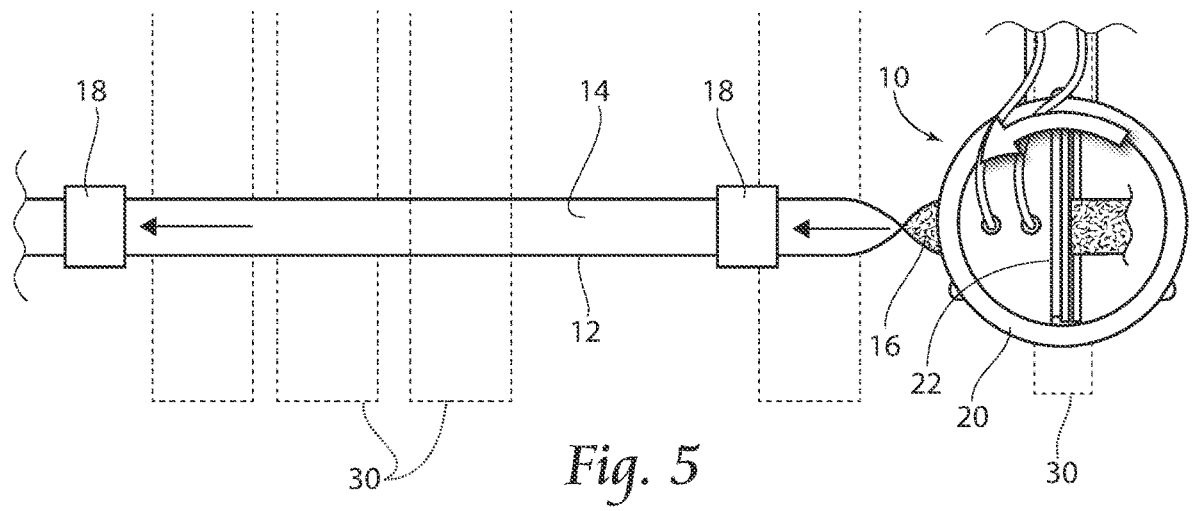
FIG. 5 shows the twisted web correction migrating downstream after the web correction sequence has been performed.
Figure 6:
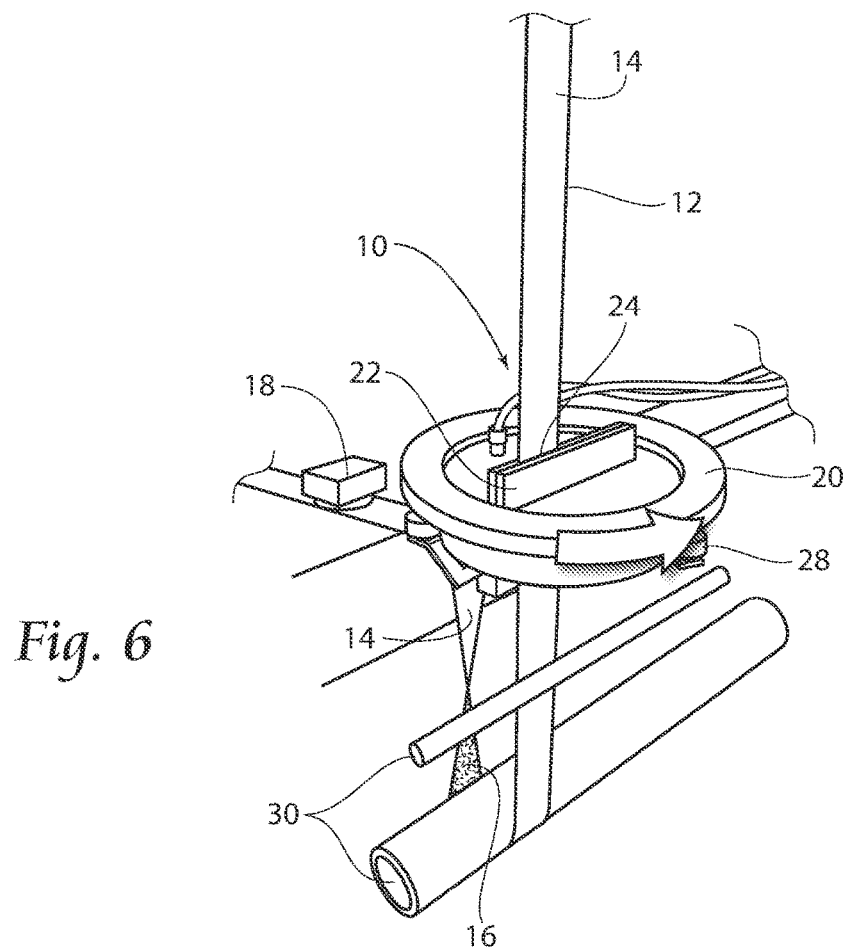
FIG. 6 is a perspective view of the condition shown in FIG. 5.
Figure 7:
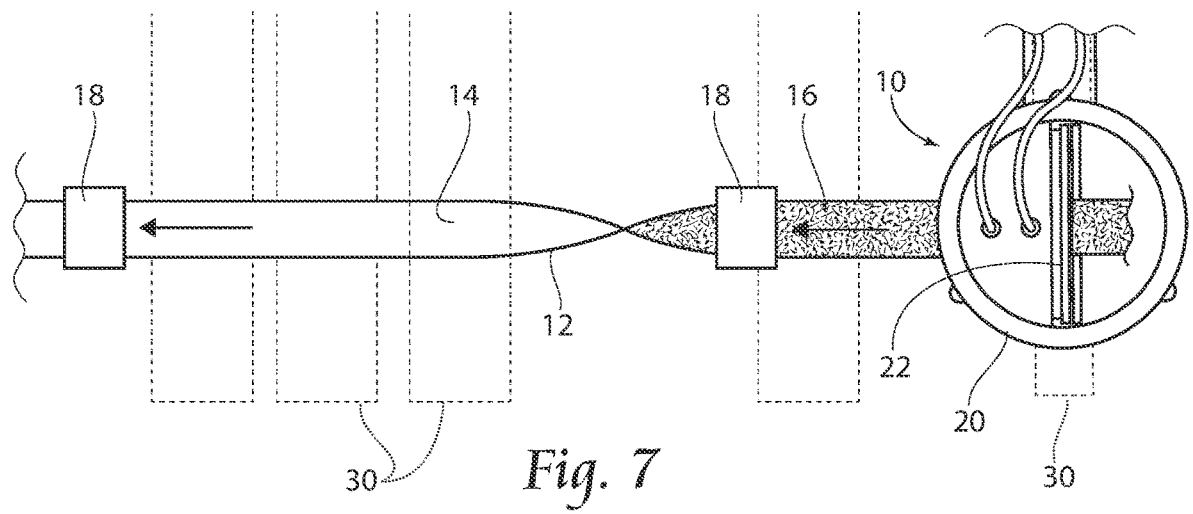
FIG. 7 shows the twisted web correction continuing to migrate downstream after the web correction sequence has been performed.

This condition will be detected by detection (vision) stations 18, which would detect the presence of incorrect side 14 of the web 12 (as opposed to side 16) and reported to the PLC, which will initiate, as shown in FIGS. 3 and 4, a top and perspective view of the web processing system initiating a correction sequence. In the correction sequence, the ring 20 is rotated 180 degrees either clockwise or counterclockwise, but in the case of FIG. 3, counterclockwise.

Figure 8:
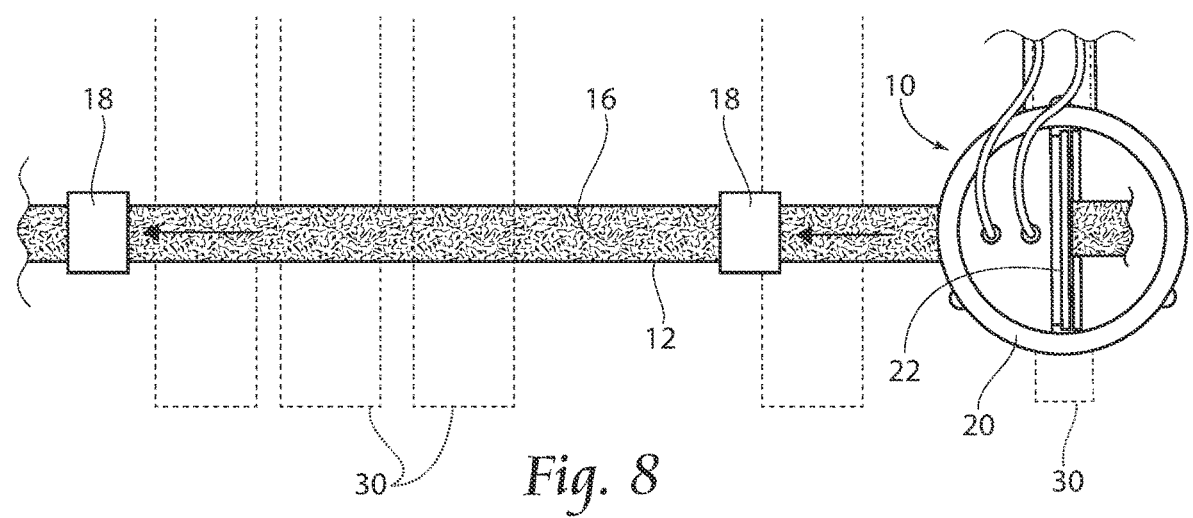
FIG. 8 shows the twisted web correction having been eliminated, and the web returned to its proper orientation, after the web correction sequence has been performed.

As shown in FIGS. 4-8, the correction sequence will result in an inversion of the web by introducing a counter-twist downstream of the ring 20, which will then pass in migratory fashion downstream as more web material 12 is pulled through the system, until finally in FIG. 8, the twisted web condition is eliminated downstream. In this condition, web 12 has been restored to its proper orientation, after the web correction sequence has been performed.

Figure 9:
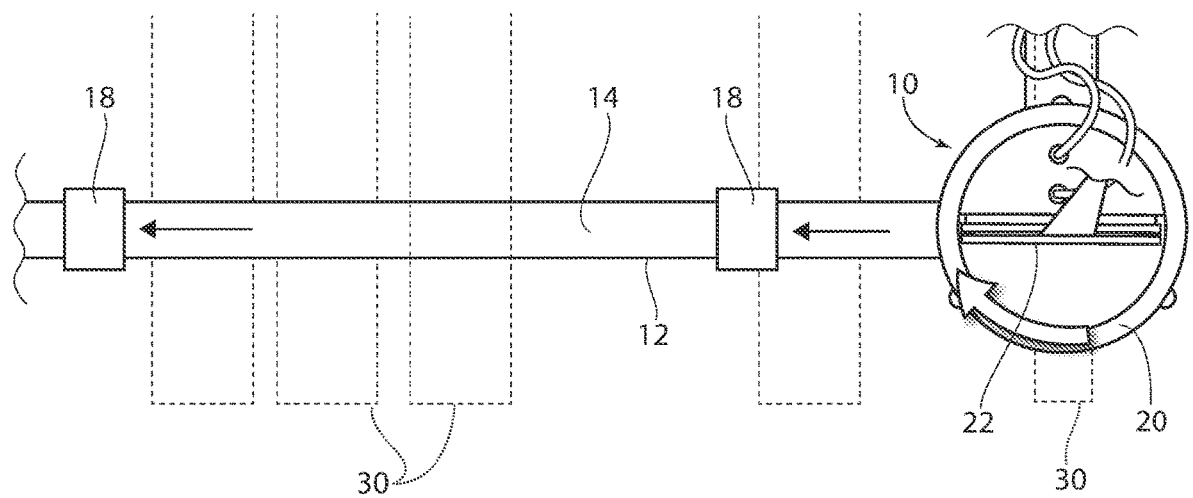
FIG. 9 is a top view of a new twist occurring in the web.
Figure 10:
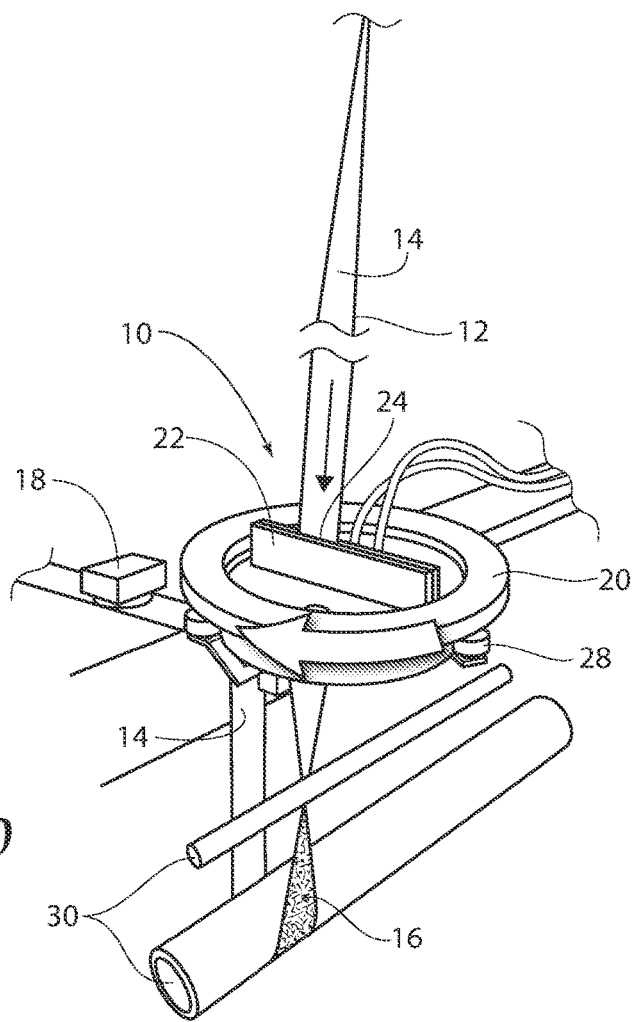
FIG. 10 is a perspective view of the twist of FIG. 9.
Figure 11:
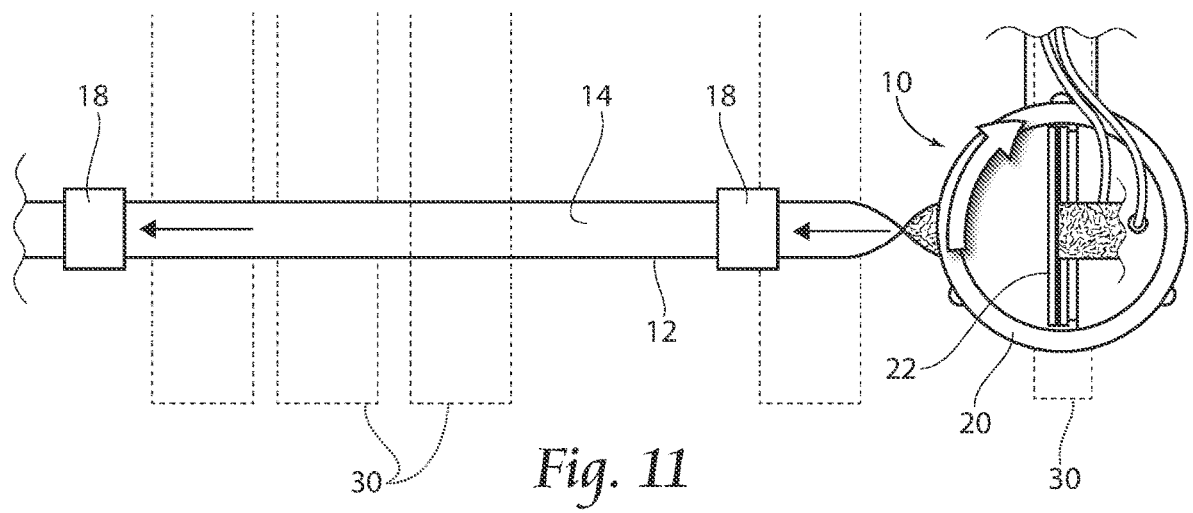
FIG. 11 is a top view of the web correction sequence again being initiated, and the correction traveling downstream.
Figure 12:
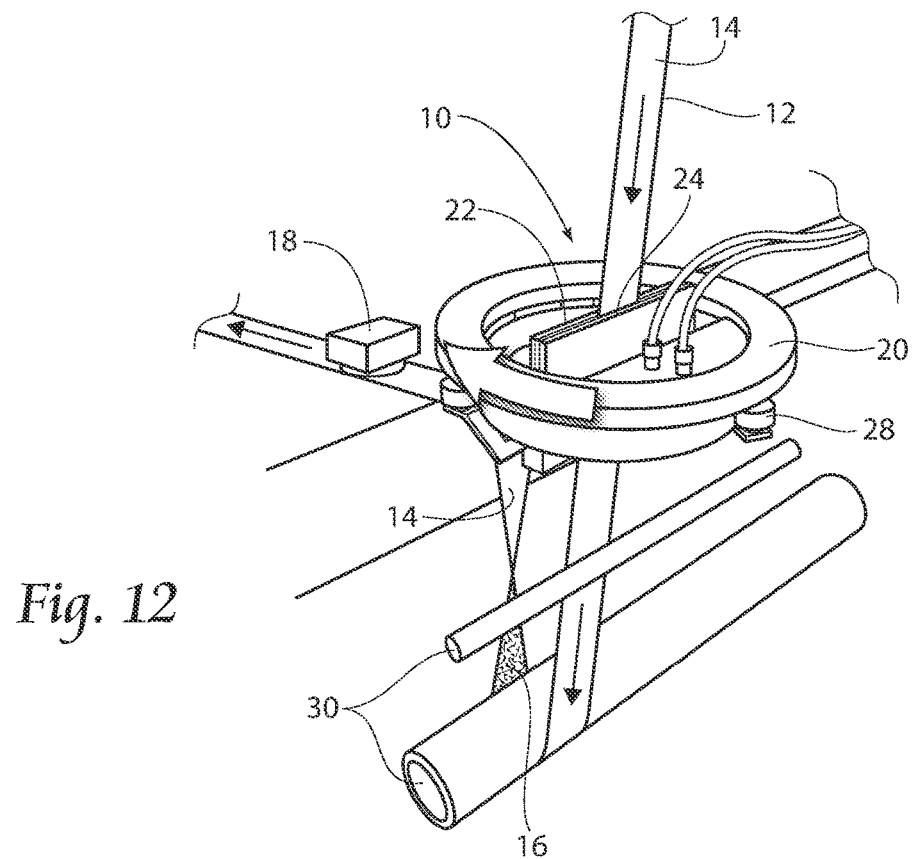
FIG. 12 is a perspective view of FIG. 11.
Figure 13:
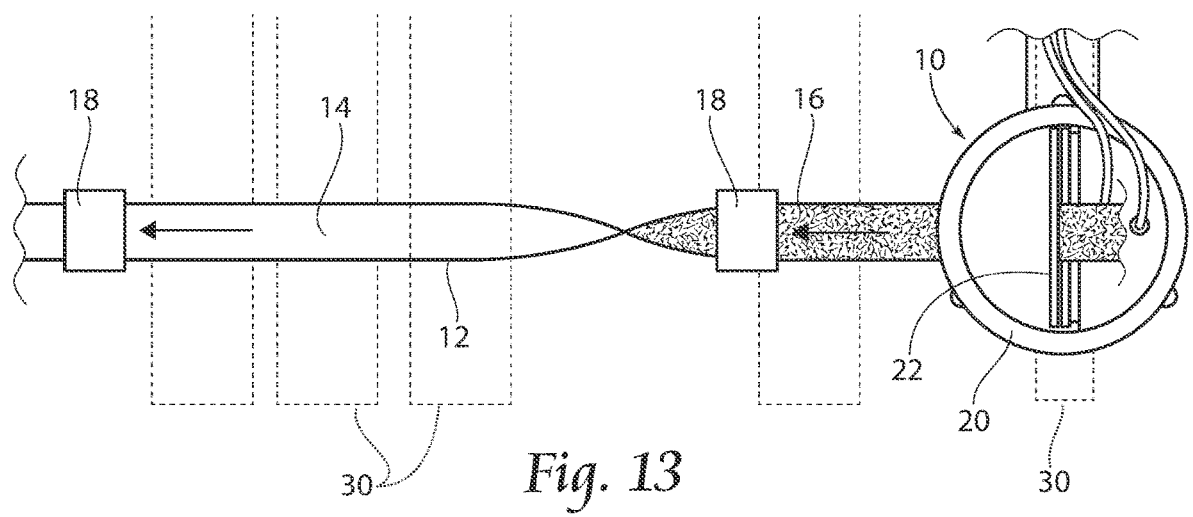
FIG. 13 is a top view of the web correction sequence with web the correction traveling downstream.
Figure 14:
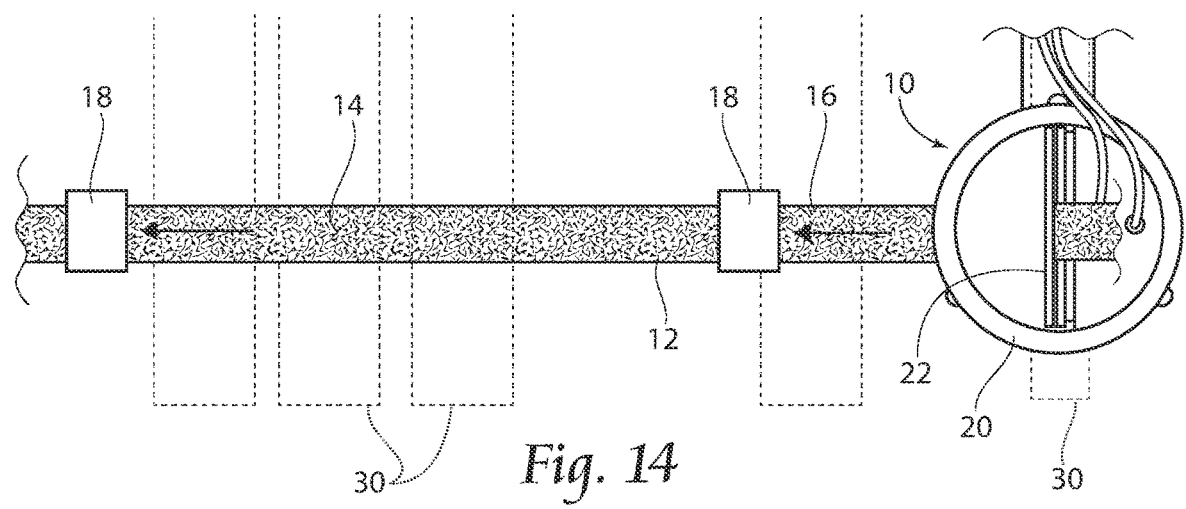
FIG. 14 is a top view of the twisted web correction having been eliminated, and the web returned to its proper orientation, after the web correction sequence has been performed.

After performing the correction sequence, diagnostics can continue to be performed in regular run mode to indicate whether the product continues meets acceptable criteria. If so, discrete elements, such as the core, tissue layers, elastic, etc., continue to be applied in a sequence as desired until, as shown in FIG. 9, a new twist occurs in the web 12 as indicated by the visibility of side 14 of web 12. At this point, the correction sequence is again triggered by the vision system 18 as previously described. Preferably (although not required), in alternating correction sequences, the ring 20 is rotated counterclockwise (FIGS. 3-8) and clockwise (FIGS. 9-11). This is done in order to minimize the amount of twist imparted upstream of the ring 20, although some amount of upstream twist is tolerable in the system.

FIGS. 10-14 show the correction sequence again being accomplished, this time in clockwise fashion with the result once again that the web is returned to its properly oriented condition.

The vision and data tracking and control is fully disclosed in U.S. application Ser. No. 11/880,261, which is incorporated herein by reference.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An apparatus for orienting an incoming web having a first side and a second side to a predetermined orientation of the first side relative to the second side, wherein an image of the first side as imaged with a camera is different from an image of the second side as imaged with a camera, the apparatus comprising:
   a rotatable web guide configured to pass the incoming web therethrough;
   a lighting system configured to highlight features of the incoming web that differentiate the first side from the second side;
   a vision system having a camera configured to capture an image of either the top side or the bottom side of an untwisted portion of the incoming web and converting the output of the camera to a two-dimensional array of numbers representing pixels corresponding to luminous intensity levels at points in the image;
   a controller configured to:
      process the image captured by the vision system by thresholding each of the pixels in the array to provide a two-dimensional array of light and dark pixels;
      evaluate the two-dimensional array of light and dark pixels to determine whether the image captured is of the first side or the second side of the incoming web;
      if the incoming web is not in the predetermined orientation, control the rotatable web guide to introduce a twist in the incoming web to orient the incoming web in the predetermined orientation.

2. The apparatus of claim 1, wherein the vision system is positioned downstream of the rotatable web guide.

3. The apparatus of claim 1, wherein the controller, in being configured to introduce the twist, is configured to rotate the rotatable web guide in a first direction.

4. The apparatus of claim 3, wherein the controller, in being configured to introduce the twist, is configured to rotate the rotatable web guide 180 degrees in the first direction.

5. The apparatus of claim 3, wherein the controller is further programmed to introduce a subsequent twist in the incoming web; and
   wherein the controller, in being configured to introduce the subsequent twist, is configured to rotate the rotatable web guide in a second direction opposite of the first direction.

6. The apparatus of claim 3, wherein the controller is further programmed to introduce a plurality of subsequent twists in the incoming web; and
   wherein the controller, in being configured to introduce the plurality of subsequent twists, is configured to alternate rotation of the rotatable web guide between the first direction and a second direction opposite of the first direction for successive subsequent twists.

7. The apparatus of claim 1, wherein the rotatable web guide comprises a pair of guide plates having an open condition and a closed condition;
   wherein, in the closed condition, the pair of guide plates is configured to effectuate the twist in the incoming web; and
   wherein, in the open condition, the pair of guide plates is configured to allow splices in the incoming web to pass.

8. The apparatus of claim 7 further comprising a plurality of pneumatic air lines configured to actuate the pair of guide plates between the open and closed conditions.

9. An apparatus for orienting an incoming web having a first side and a second side to a predetermined orientation of the first side relative to the second side, wherein an image of the first side is different from an image of the second side as imaged with a camera, the apparatus comprising:
   a rotatable web guide configured to pass the incoming web therethrough;
   a vision system configured to capture an image of a top side or a bottom side of the incoming web oriented as passed through the rotatable web guide and to convert the image to a two-dimensional array of pixels representing the image;
   a controller configured to:
   process the image captured by the vision system by thresholding each of the pixels to provide a two-dimensional array of light and dark pixels;
   determine whether the image captured is of the first side or the second side based on an analysis of a plurality of the pixels in the two dimensional array of light and dark pixels;
   if the incoming web is not in the predetermined orientation, controlling the rotatable web guide to flip the incoming web to the proper orientation.

10. The apparatus of claim 9, wherein the vision system is positioned downstream of the rotatable web guide.

11. The apparatus of claim 9, wherein the controller is configured to rotate the rotatable web guide in a first direction.

12. The apparatus of claim 11, wherein the controller is configured to rotate the rotatable web guide 180 degrees in the first direction.

13. The apparatus of claim 11, wherein the controller is further programmed to introduce a plurality of twists in the incoming web to flip the incoming web to the proper orientation; and
wherein the controller is configured to alternate rotation of the rotatable web guide between the first direction and a second direction opposite of the first direction for successive twists.

14. A method of orienting a running web to a predetermined orientation of the first side relative to the second side, wherein the first side is different from the second side as visualized by a camera, the method comprising:
illuminating the web to highlight features of interest that differentiate the first side from the second side;
capturing an image of a top side or a bottom side of the running web in an image capture zone and converting the output of the camera to a two-dimensional array of numbers representing the image;
processing the two-dimensional array by thresholding the two-dimensional array to identify light and dark pixels and analyzing the light and dark pixels to determine whether the image is of the first side or the second side by identifying the highlighted features of interest;
determining whether the running web is in the predetermined orientation in the image capture zone; and
if the first side is not in the predetermined orientation in the image capture zone, actuating a rotatable web guide to flip the running web to reorient the first side relative to the second side.

15. The method of claim 14, wherein actuating the rotatable web guide comprises causing the rotatable web guide to rotate in a first direction in an amount of rotation sufficient to orient the web to the predetermined orientation.

16. The method of claim 15, wherein the amount of rotation comprises 180 degrees.

17. The method of claim 15 further comprising:
determining whether the running web has rotated away from the predetermined orientation after actuating the rotatable web guide; and
if the running web has rotated away from the predetermined orientation, actuating the rotatable web guide to rotate in a second direction in the amount of rotation sufficient to reorient the running web to the predetermined orientation.

18. The method of claim 17 further comprising alternating actuation of the rotatable web guide between the first and second directions.

19. The method of claim 14, wherein the image capture zone is downstream of the rotatable web guide.

20. The method of claim 14, wherein the rotatable web guide comprises a pair of guide plates having an open condition and a closed condition;
wherein, in the closed condition, the pair of guide plates is configured to effectuate the twist in the incoming web; and
wherein, in the open condition, the pair of guide plates is configured to allow splices in the incoming web to pass.

21. The method of claim 1, wherein the controller places the image in computer memory so that it may be later processed.

22. The method of claim 14, wherein the controller places the image in computer memory so that it may be later processed.

23. The apparatus of claim 1, wherein the controller is further configured to evaluate the two-dimensional array of light and dark pixels by counting at least one of the light and the dark pixels in the array.

24. The apparatus of claim 1, wherein the controller is further configured to evaluate the two-dimensional array of light and dark pixels by edge detection in the array.

25. The apparatus of claim 9, wherein the controller is further configured to determine whether the image is of the first or second side of the incoming web by at least one of counting at least one of the light and the dark pixels in the array or performing an edge detection process on the two-dimensional array of light and dark pixels.

26. The method of claim 14, further comprising the step of processing the two-dimensional array of light and dark pixels by counting at least one of the light and dark pixels or performing an edge detection process on the two-dimensional array of light and dark pixels.

* * * * *